April 4, 1972 A. N. ROBERTS Plant Pat. 3,093
WHITE AZALEA PLANT
Filed Feb. 9, 1970
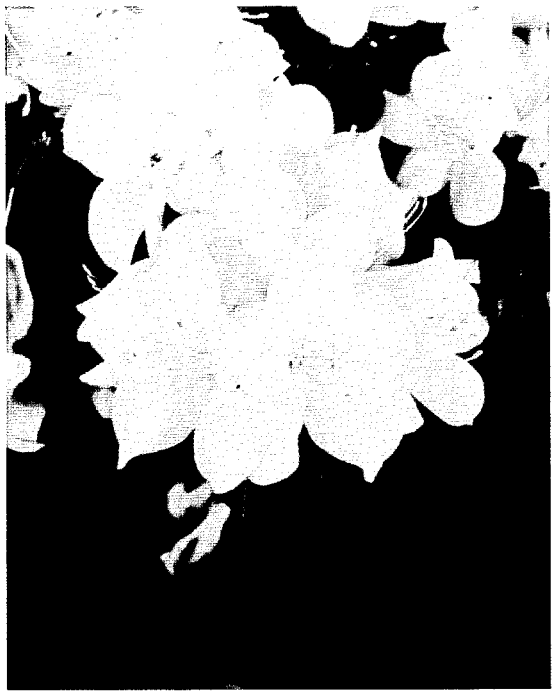
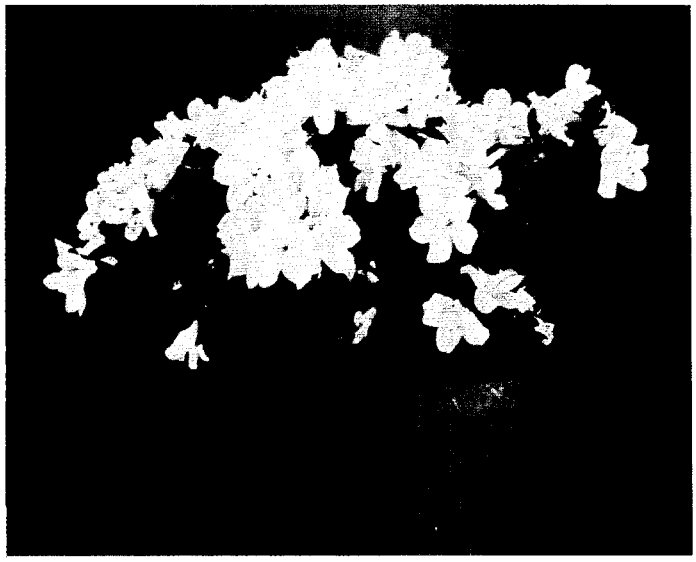
INVENTOR.
ALFRED N. ROBERTS
BY Rummler & Snow
Attys.

United States Patent Office

Plant Pat. 3,093
Patented Apr. 4, 1972

3,093

WHITE AZALEA PLANT

Alfred N. Roberts, Corvallis, Oreg., assignor to Geo. J. Ball, Inc., West Chicago, Ill.

Filed Feb. 9, 1970, Ser. No. 10,058
Int. Cl. A01h *5/00*
U.S. Cl. Plt.—55 1 Claim

ABSTRACT OF THE DISCLOSURE

A new variety of hybrid azalea plant characterized by its profuse production of white blossoms of medium size, which have excellent keeping quality, and by its vigorous, well branched growth and strength under pot forcing in greenhouse culture.

BACKGROUND OF THE INVENTION

My new variety of white azelea plant was discovered as a seedling of unknown parentage occurring in the course of breeding efforts carried on by me at Corvallis, Oreg., with the objective of producing an improved pot forcing greenhouse azalea having better flowering and keeping qualities. The new plant was observed to have many of the desired characteristics including very prolific breaking, unusual petal substance, and a very abundant blooming habit. Extensive asexual reproduction to the plants by means of cutting, at Corvallis, Oreg., has demonstrated that its novel and distinguishing characteristics are fixed and hold true from generation to generation.

Propagation of my new azalea plant on a commercial scale is now being done, by cuttings, at Salem, Oreg.; Woodburn, Oreg.; and San Fernando, Calif.; in the belief and expectation that the new variety fills a need in the market and has excellent commercial prospects.

DESCRIPTION OF THE DRAWING

The new variety of azalea plant is illustrated in the accompanying photographic drawing in which the upper view shows the blooms in close-up detail, and the lower view shows a typical specimen of a potted plant in full bloom.

DESCRIPTION OF THE NEW PLANT

The following is a detailed description of my new variety of azalea plant with color designations according to the Horticultural Colour Chart of the British Colour Council.

The plant

Origin: Seedling.
Parentage: Unknown.
Classification: Hybrid.
Form: Spreading bush.
Growth: Vigorous, upright and sturdy.
Branching: Plant is well branched.
Foliage:
*Quantity.*—Abundant
*Shape of leaf.*—Oblanceolate to spatulate
*Texture.*—Hirsute
*Color of leaves.*—Upper side—near Ivy Green 0001060/3. Under side—between Spinach Green 0960/2 and Willow Green 000862/2, Plant has no prickles.

The bud

Form: Oblanceolate.
Size: Length—1 to 1¼ inches; diameter—¼ to ½ inch.
Opening: Bud opens slowly.
Color: When sepals first divide—near Pea Green 61/3. When sepals begin to unfurl—White on upper margin, changing to Pea Green 61/3 over basal half of petal.
Sepals: Upstanding, generally rhomboidal in shape, long ciliate,
*Color.*—Inside—Lettuce Green 861/3. Outside—Lettuce Green 861/3.
Calyx: Shape—Funnelform, deeply cleft.
*Size:*—Small. Calyx splits and has a hairy aspect.
Peduncle: ¼ inch long; hairy and erect.

The flower

Blooming habit: Profusely, once a year, early Spring to Midseason.
Size: Medium, 2¼ to 2½ inches in diameter and 1¼ to 1½ inches deep.
Borne: In clusters—4 to 7 on the stem.
Shape: Funnel shaped. Petals recurve as bloom ages.
Petalage: Number of petals—usually 5.
*Form:*—Individual petals spatulate fused at base to give a general funnel form appearance. Petals are extraordinarily thick.
*Color.*—Face side—White, often stippled with Delft Rose 020/2, with base Pea Green 61/3. Reverse side—White, occasionally stippled or spotted with Delft Rose 020/2.
*Texture.*—Satiny,
*Petaloids.*—Occasionally one,
Peduncle: Sturdy and upright—¼ inch long.
Effect of weather: Not affected by hot or wet weather.
Persistence: Flower does not hang on and dry.
Lasting quality: Excellent.

Reproductive organs

Stamens: Anthers—1/16 inch long; 5, 6 or 7 in number and arranged around the style. Filaments—White in color and as long or longer than the corolla.
Pollen: Color—Primrose Yellow 601/3.
Pistils: Number—One.
Stigmas: Color—Scheele's Green 0860/3.

My new azalea plant variety differs materially from all cultivated varieties known to me, particularly with respect to its very prolific breaking, its very floriferous habit and its vigorous, well branching and spreading growth habit which makes the new plant ideally suited for greenhouse forcing. The well formed blossoms are especially distinguished by their unusually thick and satiny petals.

I claim:

1. A new and distinctive variety of azalea plant substantially as herein shown and described, characterized by its proliferous production of white blossoms, the thick firm petals of the blossoms, its vigorous well branched growth habit under pot-forcing procedures in greenhouse culture, and the excellent lasting quality of the blooming plant.

No references cited.

ROBERT E. BAGWILL, Primary Examiner